United States Patent [19]

Sköld et al.

[11] Patent Number: 5,273,718
[45] Date of Patent: Dec. 28, 1993

[54] APPARATUS FOR CARRYING OUT BIOCHEMICAL REACTIONS

[75] Inventors: Sven-Erik Sköld; Kent Andersson, both of Upsala, Sweden

[73] Assignee: Pharmacia LKB Biotechnology AB, Upsala, Sweden

[21] Appl. No.: 838,810

[22] PCT Filed: Aug. 7, 1991

[86] PCT No.: PCT/SE91/00523
§ 371 Date: Mar. 19, 1992
§ 102(e) Date: Mar. 19, 1992

[87] PCT Pub. No.: WO92/02303
PCT Pub. Date: Feb. 20, 1992

[30] Foreign Application Priority Data

Aug. 7, 1990 [SE] Sweden .................. 9002579

[51] Int. Cl.$^5$ ...................................... B01L 11/00
[52] U.S. Cl. ................................ 422/101; 422/100; 436/809; 435/310; 435/311; 435/313
[58] Field of Search ............... 422/63, 65, 67, 101, 422/100, 103; 436/47, 48, 809; 435/310, 311, 313

[56] References Cited

U.S. PATENT DOCUMENTS

| | | | |
|---|---|---|---|
| 4,246,339 | 1/1981 | Cole et al. | 422/101 X |
| 4,304,865 | 12/1981 | O'Brien et al. | 422/102 X |
| 4,493,815 | 1/1985 | Fernwood | 422/101 |
| 4,642,220 | 2/1987 | Björkman | 436/809 X |
| 4,681,742 | 7/1987 | Johnson et al. | 422/65 X |
| 4,777,021 | 10/1988 | Wertz et al. | 422/101 |
| 4,895,706 | 1/1990 | Root | 422/102 |
| 4,931,400 | 6/1990 | Jitsukawa | 435/293 X |
| 4,931,402 | 6/1990 | Abplanalp | 435/291 |
| 5,108,703 | 4/1992 | Pfost et al. | 422/65 |

Primary Examiner—James C. Housel
Assistant Examiner—Maureen M. Wallenhorst
Attorney, Agent, or Firm—Fred Philpitt

[57] ABSTRACT

An apparatus for carrying out biochemical reactions in microtiter plates includes a device (42, 43) for receiving and holding microtiter plate (44) to be processed, the microtiter plate being provided with a plurality of wells and each well having a bottom outlet, and a movably mounted device (47) for the application of gas pressure to the wells of the microtiter plate (44), the pressure device including a sealing collar (48) and being movable between a position where it leaves the upper part of the microtiter plate accessible, and a position where it sealingly contacts the microtiter plate through the sealing collar (48) so that a gas pressure may be applied to the inlets of the microtiter plate wells for pressing out liquid present therein through the bottom outlet of each well.

1 Claim, 3 Drawing Sheets

APPARATUS FOR CARRYING OUT BIOCHEMICAL REACTIONS

The present invention is related to automation of biochemical reactions, and more particularly to the treatment of a plurality of samples in microtiter plates or similar processing plates in molecular biological methods.

Molecular biology is a rapidly growing field of science but since it is a fairly young discipline a great number of basic methods are still done manually, or at best semi-automatically. This being the case in spite of the fact that many of the procedures utilized are based on handling a great number of samples, in a lot of repetitive steps. Examples of such methods include isolation of RNA, chromosomal DNA or DNA from plasmids or other vectors, restriction enzyme digestion of DNA, sequencing of DNA, elongation and polymerization of DNA by enzymes, oligonucleotide synthesis, construction of various vectors and gene libraries in microorganisms, screening of bacterial strains for biologically active clones, etc, etc. Each method of this type involves frequent manual handling of samples like for instance by the transfer of liquids between containers by pipetting, mixing, centrifugation, incubation, washing and precipitation, just to mention a few procedures.

Another general characteristic of methods in molecular biology is that some of the reagents are available only in small amounts or are very expensive, and therefore in most cases only very small volumes, usually in the $\mu l$ range, of reagents and reaction mixtures are handled in each step of such a method. The reagents or other compounds in the reaction mixtures are moreover often sensitive and therefore special precautions considering temperatures, mechanical sheering, etc, are required. Some of the methods further comprise the handling of potentially hazardous compounds.

Experimental work in molecular biology is accordingly very time consuming and labor intensive. The need for automation can be further illustrated with an example of single-stranded template preparation and DNA sequencing, according to a method described in Current Protocols in Molecular Biology, Ed. F. M. Ausbel.

So far automation in molecular biology has mainly been purification and sequencing chemistry have been automated with laboratory robotic equipments essentially automating the same procedures as they are performed manually Examples of such equipments are: Beckman Biomek 1000 and the Zymark robotic system. Although these robots have certain advantages over the manual methods there are still many drawbacks Firstly, a lot of consumables are used like for instance a new pipette tip for every liquid manipulation. Secondly, the systems are general laboratory robots and fairly complicated to use and to reprogram. Thirdly, a lot of manual work has to be carried out before as well as after the robot has been processing a part of the complete method. Sometimes a program has to be interrupted in the middle of a run and sample manually taken out for a centrifugation or incubation step. These drawbacks together with the high cost of a laboratory robot makes it far from ideal in a molecular biology laboratory.

Microtiter plates, which are trays having a number of separate reaction wells with openings on one side (the upper side) of the tray, are often used for carrying out the manual type of procedures discussed above, since a number of experiments can be carried out in parallel. Samples, liquids etc are introduced into said wells and subjected to the various procedures of the particular method. In one type of microtiter plates there is also an outlet from each well at the bottom side of the plate through which liquid can be drained from the well to a waste, for instance by suction. This outlet can be open, but preferably it contains a porous membrane for retaining particles or precipitates in the well, depending on the type of method to be carried out. A microtiter well can also be packed with a matrix for chromatographic separation of various constituents in a sample. Such matrices are mainly of the type in which components are retained by binding due to electrostatic interaction (ion exchange), hydrophobic interaction or by biospecific affinity, for instance antigen-antibody interaction, enzyme-substrate interaction, etc. Wells of this type are in fact small chromatography columns. Various types of microtiter plates are manufactured for instance by the companies Pall, Costar, Nunc and Millipore.

In U.S. Pat. No. 30,562 discloses an immunological testing device which contains a collector structure, a through-passage structure and a washing structure, for safer handling of multiple samples.

U.S. Pat. No. 4,895,706 describes a filter strip assembly comprising a first strip with a linear array of wells having open top and bottom ends and discrete filter membranes closing the bottom ends, and a second strip with wells having closed bottoms placed below the first filter strip. By the application of a pressure differential across the filter membrane, such as by vacuum, the wells of the second strip will receive the filtrate from the respective wells of the first filter strip.

CH-A-669 851 discloses a photometric analyzing apparatus comprising a movable support for a microtiter plate by which the wells of the microtiter plate may be brought into the beam path of a photometer as well as below a head member for the introduction into and removal of wash liquid from the wells. Samples are applied through a moving dispenser arm. The apparatus also comprises an incubator where microtiter plates may be stored vertically, and optionally also a storage station for prepared microtiter plates.

U.S. Pat. No. 4,493,815 discloses a biochemical test plate assembly for use in both filter assays and fluid retention applications. It comprises an upper plate with a plurality of discrete apertures, a lower plate with aligned apertures, a microporous film separating the two plates, and a base plate with a central recess to define an enclosed chamber below the lower plate, which recess has a vacuum connection.

There is however no system described, as far as we know, which offers a flexible handling of samples with the use of microtiter plates, the latter forming an excellent basis for a system for performing biochemical reactions, mainly due to their format and the comparatively high number of wells contained in each plate, and making it possible to run several experiments in parallel and the possibility to include also various matrices for the desired reactions to take place.

It is therefore an object of the present invention to provide an apparatus which offers a simplified handling and processing of microtiter plates or similar processing plates in connection with the performance of biochemical reactions, a basic concept of the invention residing in the provision of special means for the transfer of solutions or suspensions from the microtiter plate wells, and particularly from the wells of one microtiter plate to the wells of another.

According to a particular aspect of the present invention there is provided an apparatus for automatic handling of microtiter plates, complex liquid handling for providing solutions or suspensions to all or selected wells of a microtiter plate, and means for transferring reagent and sample solutions between microtiter plates, optionally also providing incubation and storage conditions at selected temperatures.

The present invention accordingly relates to an apparatus for carrying out biochemical reactions in microtiter plates comprising (i) means for receiving and holding a microtiter plate to be processed, said microtiter plate being provided with a plurality of wells and each well having a bottom outlet (either a membrane bottom or a capillary outlet), and (ii) a movably mounted device for the application of gas pressure to the wells of said microtiter plate, said device comprising sealing means and being movable between a position where it leaves the upper part of the microtiter plate accessible, and a position where it sealingly contacts the microtiter plate through said sealing means so that a gas pressure may be applied to the inlets of said microtiter plate wells for pressing out liquid present therein through the bottom outlet of each well.

In a preferred embodiment, the microtiter plate holding means is capable of holding at least two microtiter plates above each other, the wells of the two plates being aligned so that the outlet of a well in the upper plate is placed over the inlet of a corresponding well in the underlying microtiter plate to permit the transfer of liquid from the upper plate to the underlying plate when said gas pressure is applied.

An advantageous development of the apparatus comprises (i) a processing section comprising the microtiter plate holding means, the gas pressure application device, and optionally means for dispensing liquid to the wells of said upper microtiter plate, (ii) a storage rack for holding at least two microtiter plates, and (iii) means for moving microtiter plates between the rack and the processing section and optionally the incubation section.

The invention will now be described in more detail, by way of example only, with regard to illustrative embodiments of the invention. Reference will be made to FIGS. 1-4, in which.

Figure 1:
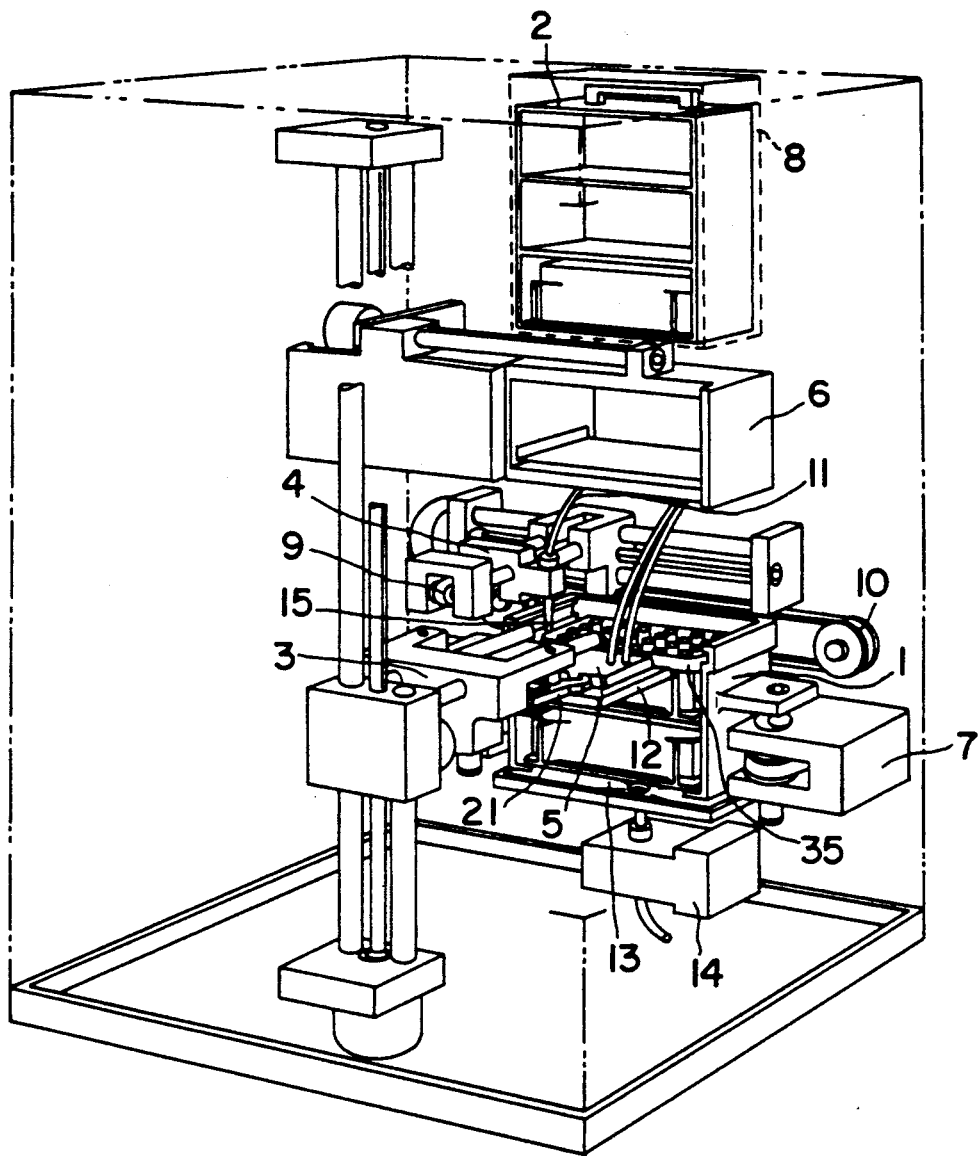
FIG. 1 is a schematic view of an embodiment of the apparatus according the invention.

The embodiment illustrated in FIG. 1 comprises the following main parts: a processing section 1; a microtiter plate storage rack 2; transfer means 3 for moving microtiter plates between the rack 2 and the processing section 1; means 4 for dispensing a solution or suspension to the wells of a first microtiter plate in the processing section 1; a pressure device 5 including means for sealingly contacting the device with a microtiter plate; an incubation section 6; and optionally means 7 for shaking the processing section 1. Control means of the apparatus preferably include a microprocessor (not shown).

Figure 2:
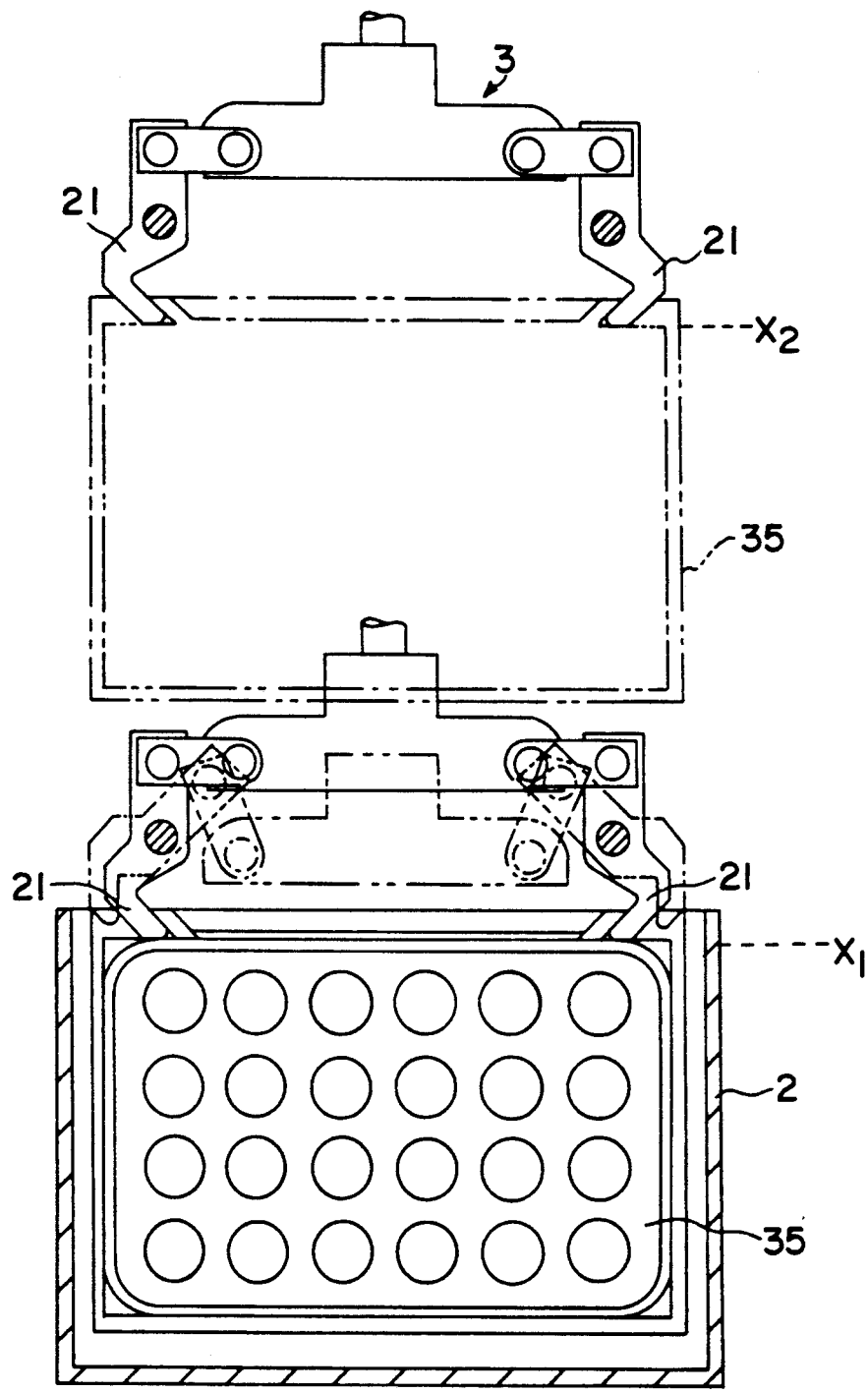
FIG. 2 is a partial sectional view illustrating the transfer means grip mechanism in the apparatus shown in FIG. 1 used for transferring microtiter plates from the rack to various sections in the apparatus.

The microtiter plate storage rack 2, in which the various plates needed for a particular application are loaded, is inserted into a compartment 8 in the apparatus. FIG. 2 shows grip means 21, supported on the transfer means 3 and used for holding a microtiter plate 35 during the transport between the rack 2 and the processing section 1. The transfer means 3 can accordingly be moved in the X-direction as well as in the in Z-direction for gripping a microtiter plate in the storage rack 2, moving it out of the rack and down to the level at which it is to be moved into the processing section 1, or vice versa. (X and Y herein define horizontal directions whereas Z is the vertical) The X-direction movement is indicated in FIG. 2 where a plate 35 is fetched in the rack 2 at position $X_1$ and moved out to the position indicated by $X_2$ at which the Z-direction movement takes place. A microtiter plate can optionally also be placed in the incubation section 6 for a predetermined time before it is further processed.

In an alternative embodiment of the invention, the storage rack 2 is moved in a shaft in the instrument so that any microtiter plate can be positioned at the level where it is to be delivered to the incubation section 6 or the processing section 1. Transfer means for moving the microtiter plates to the desired position in this case are analogous to those described above and will readily be apparent to the man of skill in the art.

The dispensing device 4, which may have several dosing tips, is placed in the processing area 1 and is constructed for adding liquid to the wells. The dispensing device 4 is movable in the X- and Y-directions by belt drive means 9 and 10, and optionally also in the Z-direction, and can add liquid to one or more of the wells at a time in any configuration. This dispensing device can be of the type known from fraction collectors or, in cases when the apparatus is constructed to allow transfer of liquid also between wells in the first microtiter plate, of the type known from autoinjectors. The dispensing device can optionally also be equipped with means for removing the last drop hanging under the dispensing tip 15, for instance by a gas stream. Pumps, for instance peristaltic pumps, supply the dispensing device 4 with the desired liquid from buffer or reagent bottles or vials via tubings 11 equipped with valves (not shown).

In order to transfer liquids from a first or upper microtiter plate 35 to a second or lower microtiter plate (not shown), the processing section 1 is provided with the above mentioned gas pressure device 5, preferably comprising a substantially planar plate 12 having at least the same length and width as the first microtiter plate 35. In FIG. 1 the gas pressure device 5, for clarity reasons, is shown under movement in the X-direction towards its operating position above the first microtiter plate 35.

Figure 3:
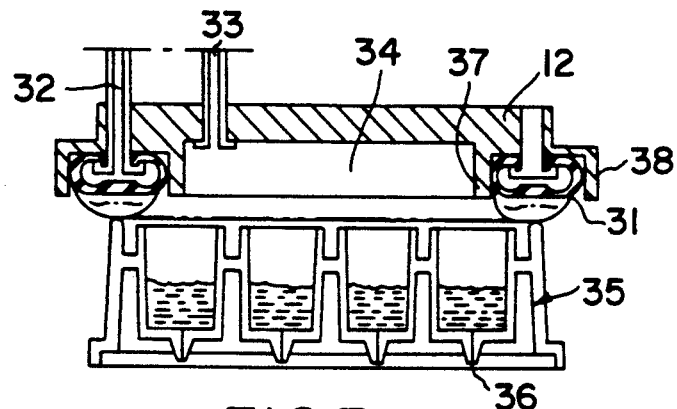
FIG. 3 is a partial sectional view illustrating the gas pressure application device of the apparatus in FIG. 1 in contact with a microtiter plate.

With reference to FIG. 3, the plate 12 has a collar 31 of an elastic material positioned between bars 37, 38 on the side of plate 12 facing the first microtiter plate 35. The collar 31 could for instance be an inflatable tubing, for example of silicon rubber, which is connected to a gas pressure source (not shown) via a channel 32. The liquid receiving second microtiter plate (not shown) is positioned in respective holding means therefor (also not shown) under the first microtiter plate with the wells of the two plates aligned so that the outlet of a well in the first plate 35 is placed over the inlet of a corresponding well in the second microtiter plate.

When the gas pressure device 5 is in its operating position an air tight connection to the first microtiter plate is obtained so that a space 34 is defined by the first microtiter plate 35, the collar 31 and the pressure device plate 12. This is achieved when the two microtiter plates are close to each other and the collar is inflated so that it contacts the microtiter plate 35. Alternatively, the two plates are simply pressed together so that the gas tight connection is obtained.

When gas pressure is applied into the space 34 via a channel 33, the solution in each of the microtiter wells is expelled out of the bottom membrane 36. If the solution from each well is to be directed to waste this could be achieved by expelling the solutions to a separate waste plate or to a waste collector 13 at the bottom of the processing section. Preferably, the microtiter plates in the processing section 1 are shaken by the shaking means 7 during processing so that a suspension can be kept suspended when the liquid is expelled from the microtiter plate.

For checking the solution expelled from a microtiter plate in the processing section, a detector unit 14 is optionally positioned after the waste collecting means 13. This is of importance for instance for checking that enough washing solution has been added to all wells in the microtiter plate or that a given reaction has taken place.

In order to mix the solutions dispensed to each well of the microtiter plates placed in the processing section 1, at least the first microtiter plate 35 is arranged to be shaken, optionally also when gas pressure is applied to the wells. This could be achieved by the above mentioned shaking means 7 causing an oscillating movement of the processing section 1. This feature is also of importance for keeping suspensions suspended in order to avoid clogging of the filter membrane at the well bottom.

The flexibility of the above described system is readily appreciated but will be further illustrated with a general description of its use in biomolecular applications, however, without limiting the scope of the invention in any way whatsoever.

The microtiter plates needed for a particular application, that is for example plates containing the samples to be processed, for instance after culture, empty receiving plates or plates containing wells prepacked with chromatography matrices or a reagent mixture, are placed in the rack 2, which is then positioned in the compartment 8. Buffer solution or reagent bottles are via tubings, pumps and valves connected to the dosing or dispensing device 4 in the processing area or section 1. A selected reagent solution can then be pumped into any one of the wells of a top microtiter plate in the processing section. Reagents can also be supplied from wells of a microtiter plate which is loaded into the storage rack. Such a reagent microtiter plate is for delivery of solution positioned as the upper or first plate in a stack configuration in the processing section as earlier described, and when gas pressure is applied the reagent is expelled to the adjacent microtiter plate next below.

Next, the microprocessor is programmed for the actual method to be carried out or an already existing method is called upon or loaded into the processor. Basic parameters for input into the program are: (i) the position of each specific microtiter plate in the storage rack, (ii) the selection of plates which should form the stacked combination of plates in the processing section during each step of the procedure to be carried out, (iii) the volume and time for addition of reagents or other liquids like buffer solutions to a given combination of wells in the first microtiter plate, (iv) time and optionally temperatures for incubation and processing, (v) time for transferring solution from wells in an upper plate to a lower plate or to waste by gas pressure, (vi) shaking time and frequency, as required by the actual application.

Figure 4:
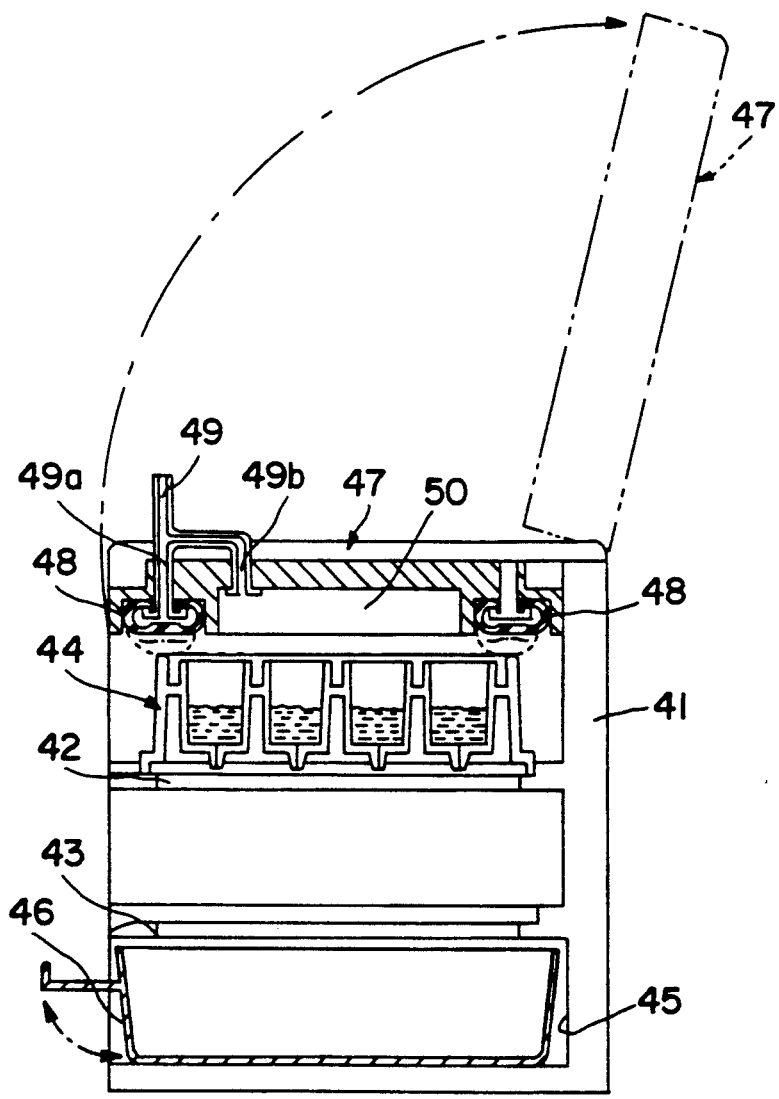
FIG. 4 is a schematic sectional view of another embodiment of the apparatus according to the invention.

FIG. 4 schematically illustrates a simplified embodiment of the invention. It comprises a box-like frame 41 enclosed by a casing (not shown) and having upper and lower holding means 42 and 43, respectively, for supporting two microtiter plates in a stacked relationship, only a microtiter plate 44 received by the upper holding means 42 being illustrated. Of course, further holding means for receiving, say, one or two additional microtiter plates may be provided. A compartment 45 is provided at the bottom of the frame 41 for holding a removable waste container 46. Movably mounted, for example hinged as shown in FIG. 4, to the top part of frame 41 is a pressure device 47, substantially identical to pressure device 5 shown in FIG. 3. This pressure device 47 thus also is of plate configuration and has an inflatable sealing collar 48, gas supply channels 49a and 49b, connected to a main supply conduit 49, and a gas application space 50. The inflated state of collar 48 is shown in dashed lines. When the pressure device 47 is swung to its "open" position, illustrated by dashed lines in the figure, the wells of microtiter plate 44 are accessible, for example for the addition of reagent solutions thereto. By swinging the pressure device 47 down to the "closing" position so that the sealing collar 48 contacts the microtiter plate 44 and then applying gas pressure, liquid in the wells will be expelled to the waste container 46 or to the wells of an underlying microtiter plate in analogous manner as described for the embodiment of FIGS. 1 to 3. Reagent solution may, of course, also in this case be added to the microtiter plate wells by placing a reagent plate on the upper holding means 42 and the receiver microtiter plate on the lower holding means 43, and expelling the reagent solution into the wells of the microtiter plate by applying gas pressure to the reagent plate wells by means of the pressure device 47. Optionally, the apparatus in FIG. 4 comprises heating means so that the microtiter plates may be incubated at a desired temperature.

The invention is, of course, not restricted to the embodiments specifically described above and shown in the drawings, but many modifications and changes may be made without departing from the scope of the inventive concept as defined in the following claims.

What is claimed is:

1. An apparatus for carrying out biochemical reactions in microtiter plates which comprises
   (a) a holder (42, 43) for receiving and holding a microtiter plate (35; 44) that is provided with a plurality of separate wells, each well having an inlet opening and a bottom outlet to expel liquid in the wells, and
   (b) a movably mounted device (5; 47) for applying gas pressure to the wells of said microtiter plate (35; 44), said gas pressure application device (5; 47) comprising a plate member (12) of at least the same length and width as said microtiter plate (35; 44), said late member (12) having an inflatable collar (31; 48) of an elastic material around the periphery facing the periphery of said microtiter plate and being adapted to sealingly connect the gas pressure application device (5; 47) over the microtiter plate so as to thereby form a single gas application space (34; 50) defined by the microtiter plate (35; 44), the inflatable collar (31; 48) and the plate member (12; 47), whereby the same pressure will be quickly and simultaneously applied to the inlet openings of all wells.

* * * * *